United States Patent [19]
Scott

[11] Patent Number: 5,329,644
[45] Date of Patent: Jul. 19, 1994

[54] DISPOSABLE URINE CONTAINER

[76] Inventor: Mary V. Scott, P.O. Box 446, Dayton, Wyo. 82836

[21] Appl. No.: 31,719

[22] Filed: Mar. 15, 1993

[51] Int. Cl.⁵ .............................................. A47K 11/12
[52] U.S. Cl. ...................................... 4/144.2; 4/144.3; 220/350; 229/125.12
[58] Field of Search .................... 4/144.1, 144.2, 144.3, 4/144.4; 220/350; 229/129.12; 383/2, 120

[56] References Cited

U.S. PATENT DOCUMENTS

| | | | |
|---|---|---|---|
| 2,690,216 | 9/1954 | Scott | 220/350 |
| 3,282,621 | 11/1966 | Peterson | 383/67 X |
| 3,421,506 | 1/1969 | Webb | 4/144.3 X |
| 3,680,543 | 8/1972 | Cox | 4/144.1 X |
| 3,929,412 | 12/1975 | Villari | 4/144.1 X |
| 4,991,979 | 2/1991 | Strand et al. | 383/67 X |

FOREIGN PATENT DOCUMENTS

| | | | |
|---|---|---|---|
| 0017507 | of 1889 | United Kingdom | 229/125.12 |
| 0106213 | 5/1917 | United Kingdom | 4/144.1 |
| 2099297 | 12/1982 | United Kingdom | 4/144.1 |
| 2188545 | 10/1987 | United Kingdom | 4/144.1 |

*Primary Examiner*—Robert M. Fetsuga
*Attorney, Agent, or Firm*—Douglas M. Clarkson; Risto A. Rinne

[57] ABSTRACT

A portable urine container for females is described as having an enclosure with concavely curved upper side portions defining an opening to provide access. A flexible, slidable tab closure is affixed around the opening and provides access to the interior of the enclosure when in an open position and effectively seals the enclosure when in a closed position. The enclosure can readily include an absorbent material to absorb fluids and to prevent a splash back of urine.

13 Claims, 1 Drawing Sheet

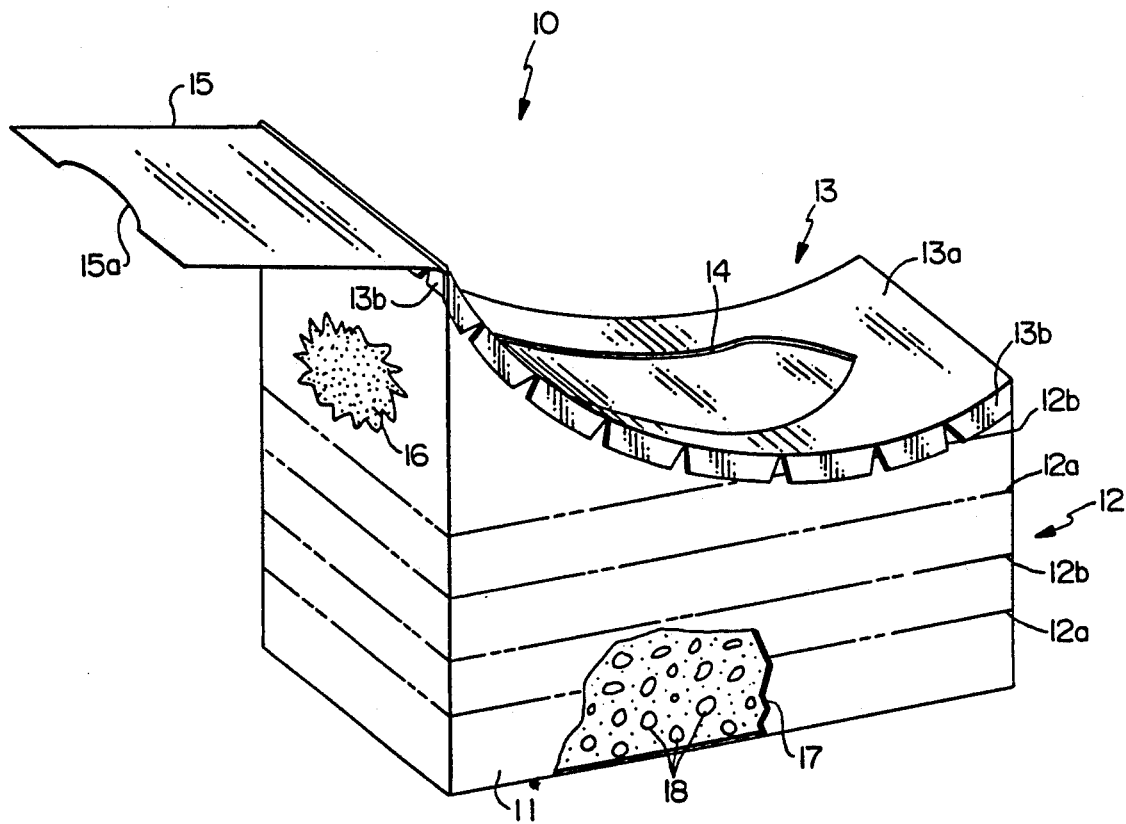

DISPOSABLE URINE CONTAINER

BACKGROUND OF THE INVENTION

1. Field of the Invention:

The present invention, in general, relates to portable toilets and, more particularly, to portable, disposable devices used to collect urine.

Such devices are more commonly referred to as portable urinals. Portable urinals, generally, are known and come in a variety of sizes and configurations. Clearly, the need for such devices is readily obvious to anyone who has ever had the experience of having a full bladder while being distant from rest room facilities.

Present portable urinals tend to be somewhat expensive to purchase and, therefore, are often reused. Since the cleaning of a portable urinal is not an especially pleasant task, the need to reuse such a device is considered to be a detriment to their sale.

Certain portable urinals which are disposable also tend to be somewhat expensive. Certain others are large and bulky, which increases their visibility and, also, detracts from their ease of portability. To many people, being seen in public with a portable urinal is an embarrassment to be avoided.

Other portable urinals tend to be difficult either to set up for use, to easily expel the urine from the body into the urinal without splash or spillage, or then to seal the device in order to retain the urine safely for disposal later.

Many of the known types of portable urinals do not properly accommodate the unique anatomical requirements of women. Those that do, rely upon contoured anatomical adapters which, typically, are then inserted into the end of a larger container and are used as an entry spout to conduct fluids into the container.

The use of an adapter by a woman is a detriment, since it tends to be rigid and bulky and is difficult to carry about inconspicuously. Furthermore, prior to using a urinal with a female-type adapter, an additional assembly step of having to insert the adapter into the end of a container, is required.

Accordingly, there exists today a need for a disposable urinal that is inexpensive to manufacture, portable, easy to use, suitable for use by either gender, and is inconspicuous to carry about.

2. Description of Prior Art:

Portable urinals, generally, are known. For example, the following United States patents describe various types of containers that are useful for collecting urine:

| | | |
|---|---|---|
| 3,329,973 | Bobbe | July 11, 1967; |
| 3,597,770 | Jacuzzi | August 10, 1971; |
| 3,600,719 | Karr | August 24, 1971; |
| 3,629,873 | Long | December 28, 1971; |
| 3,731,869 | Griffin | May 8, 1973; |
| 3,746,240 | Flynn | July 17, 1973; |
| 5,007,116 | Yamamoto | April 16, 1991; |
| 5,065,459 | Tjahaja et al. | November 19, 1991. |

While the structural arrangements of the above described devices, at first appearance, have similarities with the present invention, they differ in material respects. These differences, which will be described in more detail hereinafter, are essential for the effective use of the invention and which admit of the advantages that are not available with the prior devices.

OBJECTS AND SUMMARY OF THE INVENTION

It is an important object of the present invention to provide a disposable urine container that is inexpensive to manufacture.

It is also an object of the invention to provide a disposable urine container that is compact, collapsible and, hence, is readily portable.

Another object of the present invention is to provide a disposable urine container that can accommodate the special anatomical requirements of women.

Yet another object of the invention is to provide a disposable urine container that seals urine effectively until the container can be disposed of conveniently.

Briefly, a disposable urine container that is constructed in accordance with the principles of the present invention has a leak resistant collapsible container which has an access opening. A sliding tab seal assembly having a first open position that is used when depositing urine into the container and a second closed position that is used to retain the urine that has been deposited into the container is attached to the container surrounding the opening.

BRIEF DESCRIPTION OF THE DRAWINGS

Other objects, features and advantages of the invention will become more readily apparent from the following detailed description of the presently preferred embodiment, which is described in conjunction with the single FIGURE of drawings which is a view in perspective of a disposable urine container that is constructed in accordance with the invention.

DETAILED DESCRIPTION OF THE INVENTION

Referring to the single FIGURE of the drawings, a disposable urine container is identified generally by the numeral 10. A leakage resistant enclosure 11 is a generally rectangular shaped solid receptacle having a hollow interior for containment of urine.

Ideally, the enclosure 11 is formed so as to be water "proof". However, this is not essential since the disposable urine container 10, after use, is usually disposed of promptly.

It is only necessary that the enclosure 11 provide for the containment of urine until the container 10 can be disposed of conveniently. As such, a leak "resistant" material can frequently be used satisfactorily for the construction of the enclosure 11.

A variety of materials are suitable for construction of the enclosure 11. For example, the enclosure 11 can be fabricated quite effectively using any heavy wax impregnated paper stock that is available commercially. A wax impregnated hard-board stock can be used for even greater rigidity of the enclosure 11, as needed.

Another material that can be used effectively for construction of the enclosure 11 is a mylar material. The mylar selected can be of any desired thickness and can even be opaque, if so desired.

Special requirements can require the use of a transparent material, and mylar is particularly well suited for that use. For example, as desired the enclosure 11 is formed of a sterile and transparent mylar material when urine collection is required for medical analysis. Such a transparent enclosure is well suited when it is necessary to verify that a sufficient quantity of urine has been collected.

In addition to being leakage resistant, the enclosure 11 must also be collapsible to achieve the necessary requirement of providing inconspicuous portability. To provide an easier collapse of the fairly stiff wax impregnated paper enclosure 11, fold lines, identified generally by the reference numeral 12, are pressed into and around the sides of the enclosure 11 during manufacture.

The fold lines 12 predispose the enclosure 11 sides to bend more readily in a direction toward which each fold line 12 is pressed initially. Therefore, alternate fold lines 12a are pressed, during manufacture, from one side of the material that is to be formed into the enclosure 11, while intermediate and adjacent fold lines 12b are pressed from the opposite side of the material.

As many fold lines 12 are pre-formed in the sides of the enclosure 11 as is necessary to allow the enclosure 11 to collapse in an accordion fan fold manner when a compressive force is applied across the top and bottom of the disposable urine container 10. The disposable urine container 10 is collapsed during manufacture and is expanded by a purchaser prior to use.

Regardless of a particular material for the enclosure 11, it is collapsed during manufacture for greater ease of portability, although fold lines are not essential in every instance.

A sliding tab seal assembly identified, generally, by the reference numeral 13 is attached around the opening of the enclosure 11 by an adhesive or by the application of heat to affix the seal assembly 13 to the enclosure 11. The seal assembly 13 contains two layers, a top layer 13a and a similarly shaped bottom layer (not visible), and these layers are laminated about their peripheries, leaving a space between them for movement of a pull tab 15.

A border 13b is a part of the tab seal assembly 13 to affix it to the sides of the enclosure 11.

The top seal 13a and the bottom seal have an opening 14. The top seal opening 14 is aligned directly over the bottom seal opening (not shown). The preferred shape of each opening 14 is generally oval to better accommodate a woman's anatomical requirements during urination.

Located in the space between the top seal 13a and the bottom seal is the pull tab 15, shown in the drawing in the closed position which causes it to be visible through the top opening 14. The pull tab 15, when closed, effectively blocks the top opening 14, preventing access to the interior of the enclosure 11 and, also, preventing a liquid in the container 10 from leaking out.

The pull tab 15 fits tightly, but slidably, between the top seal 13a and the bottom seal and, when closed, forms a seal to contain any fluid in the enclosure 11.

The pull tab 15 contains an exposed end 15a which can be readily grasped and pulled, and when pulled, the tab 15 will slide, generally, out of the container 10. A fold in the end of the tab forms a protrusion that is located at the opposite end from the exposed end 15a. The protrusion prevents the pull tab 15 from being withdrawn completely out of the container 10.

The top edge of the sides of the container 10 that form the opening are curved to provide a contour more amenable to a woman's anatomy. The sliding tab seal assembly 13 also forms a generally curved surface that is in harmony with the shape provided by this curvature.

The exposed end 15a of the pull tab 15 is folded down against the end of the enclosure 11 and is attached by an adhesive 16. The exposed end 15a has accordion type folds pressed into it to allow it to collapse in harmony with the fold lines 12 of the enclosure 11.

To use the disposable urine container 10, the exposed end 15a of the pull tab 15 is grasped and pulled. The adhesive 16 is easily overcome allowing the end 15a to be separated from the end of the container 10. The adhesive 16, however, retains a residual amount of its adhesive qualities.

After use, the tab 15 is pushed back into the closed position, closing the opening 14, and the end 15a is folded down into contact with the adhesive 16.

According to a modification, the adhesive 16 is formed of an adhesive film that is attached to the end of the enclosure 11. The adhesive film has a protective tape covering that is placed over the adhesive film to protect it and is peeled back after urination to expose the adhesive film. The exposed end 15a then is pressed against the adhesive film to secured it in place.

A small cut-away section 17 of the enclosure 11 side shows a quantity of a liquid absorptive filler 18. The liquid absorptive filler 18 is used to absorb a portion of the urine that is in the container 10.

The liquid absorptive filler 18 is selected not only for its absorptive qualities, but also to attenuate the kinetic energy of the urine being expelled into the container 10 during urination. Because the container 10 is small, splash back of the urine during urination onto the user might occur otherwise. The filler 18 attenuates this kinetic energy and, then, absorbs a portion of the urine. Therefore, the filler 18 functions as a "splash resistant" filler as well.

A variety of materials are available for use as the liquid absorptive filler 18. Preferred types, of course, are those that are biodegradable, because the disposable urine container 10 of the invention is disposed of normally as refuse following its use and, typically, is deposited ultimately in a land fill. As an example of a simple, light weight, inexpensive and biodegradable liquid absorptive filler 18, crushed corn cobs are used.

The invention has been shown, described and illustrated in substantial detail with reference to the presently preferred embodiment. It will be understood by those skilled in this art that other and further changes and modifications may be made without departing from the spirit and scope of the invention which is defined by the claims appended hereto.

What is claimed is:

1. A portable urine container, comprising:
  (a) a leak resistant collapsible enclosure means for holding a predetermined quantity of urine and including opposing side wall portions with upper end portions having a concave curvature adapted for cooperation with a woman's anatomy during urination;
  (b) said enclosure means having an opening to provide access to said enclosure means;
  (c) seal means for blocking said opening and having a slideable closure to define a closed position and an open position, said seal means including a laminate arrangement of component parts that are adaptable to conform to said predetermined curvature; and
  (d) said seal means being affixed around said opening for providing access to said enclosure during urination when said slidable closure means defined said open position and to substantially seal said opening when said slidable closure means defines said closure position.

2. The portable urine container of claim 1 wherein said enclosure means includes means forming an accordion fold in its sides.

3. The portable urine container of claim 1 wherein said enclosure means is formed of a wax impregnated paper material.

4. The portable urine container of claim 1 wherein said enclosure means is formed from a mylar film material.

5. The portable urine container of claim 1 wherein said laminate arrangement includes a plurality of layers, each layer having an opening, each opening being in substantial alignment with each other opening, wherein said slidable closure is disposed between said plurality of layers for defining said closed position and said open position.

6. The portable urine container of claim 5 wherein said slidable closure includes an adhesive securing means for securing said slidable closure in said closed position against said enclosure means.

7. The portable urine container of claim 1 wherein said enclosure means includes a liquid absorptive material.

8. The portable urine container of claim 7 wherein said liquid absorptive material includes a splash resistant material.

9. The portable urine container of claim 1 wherein said leak resistant collapsible enclosure means includes a splash resistance material inside said leak resistant collapsible enclosure means.

10. The portable urine container of claim 9 wherein said splash resistance material includes a liquid absorptive material.

11. The portable urine container of claim 1 wherein said seal means includes an adhesive that attaches said slidable closure to said leak resistant collapsible enclosure means.

12. The portable urine container of claim 1 wherein said seal means is attached to said leak resistant collapsible enclosure means by heat.

13. A portable urine container, comprising:
  (a) enclosure means formed of leak resistant, biodegradeable material of predetermined rectangular dimensions with ends shorter in width than sides, said sides including upper end portions having a concave contour that is adapted for cooperation with a woman's anatomy during urination, said enclosure means including a sealed bottom and a top having a contoured configuration that corresponds with said contour of said sides;
  (b) said contoured top including means defining an opening to provide access to said enclosure means;
  (c) said contoured top being formed of at least 3 layers of material, a lower layer and a top layer being sealed about their periphery and sealed to the top of said enclosure means;
  (d) an intermediate layer of said contoured top being slidable between said lower layer and said top layer for sealing said opening when in a closed position and for providing access to said enclosure means when in an open position; and
  (e) liquid absorbing material in said enclosure means for retaining at least a portion of urine said enclosure means can contain.

* * * * *